United States Patent
Bos et al.

(10) Patent No.: US 9,963,412 B2
(45) Date of Patent: *May 8, 2018

(54) ALKANE OXIDATIVE DEHYDROGENATION AND/OR ALKENE OXIDATION

(71) Applicant: SHELL OIL COMPANY, Houston, TX (US)

(72) Inventors: Alouisius Nicolaas Renée Bos, Amsterdam (NL); Ronald Jan Schoonebeek, Amsterdam (NL); Michiel Johannes Franciscus Maria Verhaak, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 24 days.

This patent is subject to a terminal disclaimer.

(21) Appl. No.: 15/101,034

(22) PCT Filed: Dec. 4, 2014

(86) PCT No.: PCT/EP2014/076546
§ 371 (c)(1),
(2) Date: Jun. 2, 2016

(87) PCT Pub. No.: WO2015/082598
PCT Pub. Date: Jun. 11, 2015

(65) Prior Publication Data
US 2016/0304432 A1    Oct. 20, 2016

(30) Foreign Application Priority Data

Dec. 6, 2013  (EP) .................................... 13196064

(51) Int. Cl.
| | |
|---|---|
| *C07C 51/21* | (2006.01) |
| *C07C 51/25* | (2006.01) |
| *C07C 5/48* | (2006.01) |
| *B01J 37/03* | (2006.01) |
| *B01J 27/057* | (2006.01) |
| *B01J 35/02* | (2006.01) |
| *B01J 37/00* | (2006.01) |
| *B01J 37/02* | (2006.01) |

(52) U.S. Cl.
CPC ........... *C07C 51/25* (2013.01); *B01J 27/0576* (2013.01); *B01J 35/023* (2013.01); *B01J 37/0036* (2013.01); *B01J 37/0236* (2013.01); *B01J 37/031* (2013.01); *C07C 5/48* (2013.01); *C07C 51/252* (2013.01); *B01J 2523/00* (2013.01); *C07C 2523/20* (2013.01); *C07C 2523/22* (2013.01); *C07C 2523/28* (2013.01); *C07C 2527/057* (2013.01); *Y02P 20/52* (2015.11)

(58) Field of Classification Search
CPC ...................................................... C07C 51/25
See application file for complete search history.

(56) References Cited

U.S. PATENT DOCUMENTS

| | | | |
|---|---|---|---|
| 3,801,634 A | | 4/1974 | Krabetz et al. |
| 4,681,674 A | * | 7/1987 | Graven ...................... B01J 8/02 208/111.01 |
| 7,091,377 B2 | | 8/2006 | Borgmeier et al. |
| 2004/0147393 A1 | | 7/2004 | Hibst et al. |
| 2010/0256432 A1 | | 10/2010 | Arnold et al. |
| 2011/0009666 A1 | * | 1/2011 | Rosen ...................... B01J 21/04 562/548 |

FOREIGN PATENT DOCUMENTS

| | | |
|---|---|---|
| CN | 1795987 A | 7/2006 |
| EP | 1479438 | 11/2004 |
| FR | 1471983 | 3/1967 |
| WO | 2003064035 | 8/2003 |
| WO | 2010096909 | 9/2010 |
| WO | 2013/164418 | † 11/2013 |

OTHER PUBLICATIONS

Harriott, "Chemical Reactor Design", Marcel Dekker, Inc., 2003, pp. 127, 128 and 210.*
Orr, Clyde, Jr. In "Application of Mercury Penetration to Materials Analysis", Powder Technology, 3 (1969/70), pp. 117-123.
International Search Report of PCT/EP2014/076546 dated Dec. 4, 2014.
Solsona et al. "Selective oxidation of propane and ethane on diluted Mo—V—Nb—Te mixed-oxide catalysts",Journal of Catalysis, Dec. 2007, pp. 271-280.
Harriott, "Chemical Reactor Design", Marcel Dekker, Inc., (2003), pp. 127, 128, 210.†

* cited by examiner
† cited by third party

*Primary Examiner* — Sudhakar Katakam
*Assistant Examiner* — Ana Z Muresan

(57) ABSTRACT

The invention relates to a process of the oxidative dehydrogenation of an alkane containing 2 to 6 carbon atoms and/or the oxidation of an alkene containing 2 to 6 carbon atoms, wherein a gas stream comprising oxygen and the alkane and/or alkene is contacted with a mixed metal oxide catalyst containing molybdenum, vanadium, niobium and optionally tellurium, and wherein the linear velocity of said gas stream is at least 10 cm/sec.

4 Claims, 1 Drawing Sheet

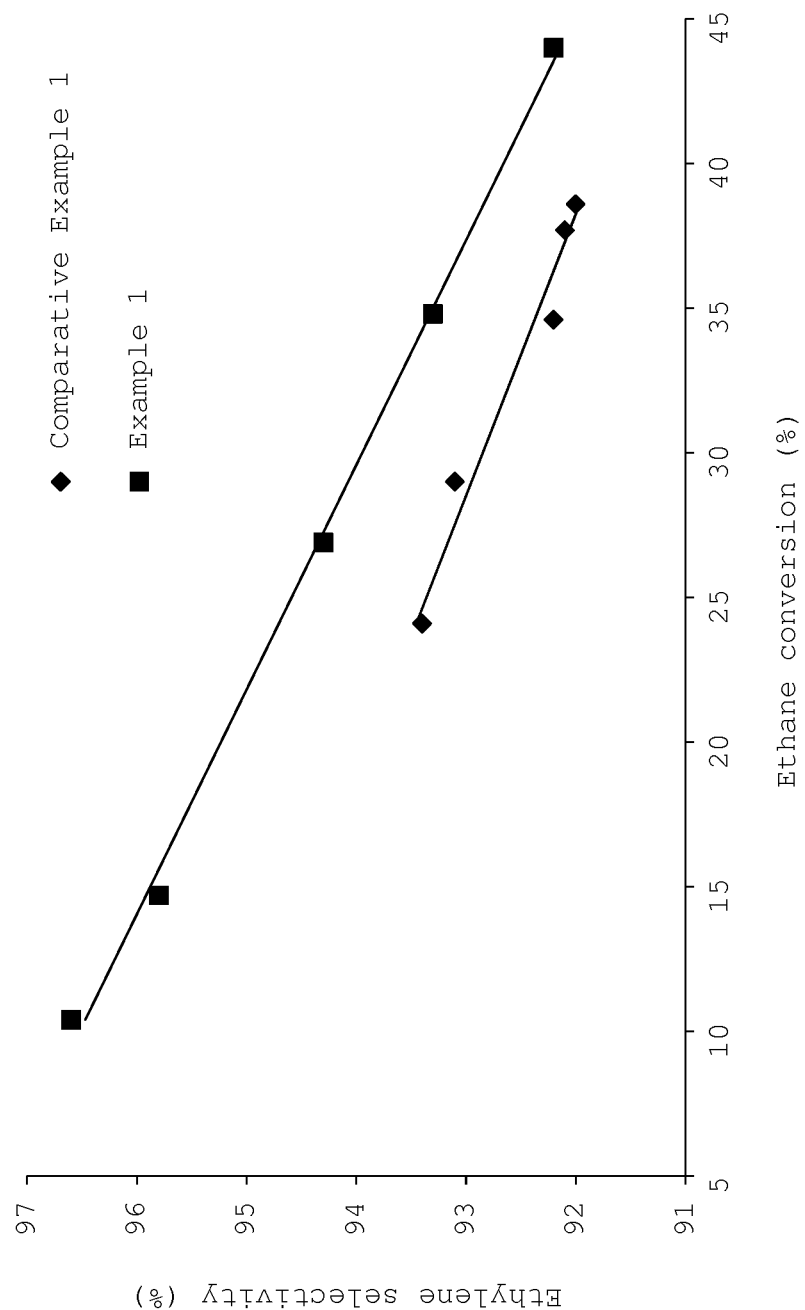

ALKANE OXIDATIVE DEHYDROGENATION AND/OR ALKENE OXIDATION

PRIORITY CLAIM

The present application is the National Stage (§ 371) of International Application No. PCT/EP2014/076546 filed Dec. 4, 2014, which claims priority from European Patent Application No 13196064.3, filed Dec. 6, 2013 incorporated herein by reference.

FIELD OF THE INVENTION

The present invention relates to a process of alkane oxidative dehydrogenation (oxydehydrogenation; ODH) and/or alkene oxidation.

BACKGROUND OF THE INVENTION

It is known to oxidatively dehydrogenate alkanes, such as alkanes containing 2 to 6 carbon atoms, for example ethane or propane resulting in ethylene and propylene, respectively, in an oxidative dehydrogenation (oxydehydrogenation; ODH) process. Examples of alkane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) as the metals, can be used as such oxydehydrogenation catalysts. Such catalysts may also be used in the direct oxidation of alkenes to carboxylic acids, such as in the oxidation of alkenes containing 2 to 6 carbon atoms, for example ethylene or propylene resulting in acetic acid and acrylic acid, respectively.

It is an objective of the present invention to provide an alkane ODH and/or alkene oxidation process, wherein a mixed metal oxide catalyst containing Mo, V, Nb and optionally Te is used, which process is performed such that a relatively high activity and/or a relatively high selectivity is or are obtained.

SUMMARY OF THE INVENTION

Surprisingly it was found that one or more of the above-mentioned objectives can be obtained by means of an alkane ODH and/or alkene oxidation process, wherein the linear velocity of the gas stream comprising oxygen ($O_2$) and the alkane and/or alkene with which stream the above-mentioned mixed metal oxide catalyst is contacted, is at least 10 centimeters (cm) per second (sec).

Accordingly, the present invention relates to a process of the oxidative dehydrogenation of an alkane containing 2 to 6 carbon atoms and/or the oxidation of an alkene containing 2 to 6 carbon atoms, wherein a gas stream comprising oxygen and the alkane and/or alkene is contacted with a mixed metal oxide catalyst containing molybdenum, vanadium, niobium and optionally tellurium, and wherein the linear velocity of said gas stream is at least 10 cm/sec.

BRIEF DESCRIPTION OF THE DRAWINGS

FIG. 1 shows a graph wherein for experiments from Example 1 and Comparative Example 1, wherein ethane ODH was performed, data for the conversion of ethane and the selectivity towards ethylene are included.

DETAILED DESCRIPTION OF THE INVENTION

In the present invention, the linear velocity of the gas stream comprising oxygen and the alkane and/or alkene through a reactor, with which the mixed metal oxide catalyst containing molybdenum, vanadium, niobium and optionally tellurium is contacted inside that reactor, is at least 10 cm/sec. It has surprisingly been found that at linear gas velocities which are lower than said 10 cm/sec, lower selectivities are obtained at the same conversion or, conversely, lower conversions are obtained at the same selectivity.

In the present invention, the mixed metal oxide catalyst containing molybdenum, vanadium, niobium and optionally tellurium is a heterogeneous catalyst in the form of particles, in other words a particulate catalyst. Preferably, said particulate catalyst (catalyst particles) is porous. Porous particles contain pores. This means that pores are present inside the porous particles. Inside the reactor, these heterogeneous catalyst particles make up a catalyst bed through which the gas stream comprising oxygen and the alkane and/or alkene is sent. In addition to catalyst particles, the catalyst bed may also contain inert (that is to say, catalytically inactive) particles.

Further, in the present invention, the linear velocity of said gas stream comprising oxygen and the alkane and/or alkene is defined as follows: linear velocity of the gas stream (in meters/second; m/s)=flow rate of the gas stream/cross-sectional surface area of the reactor/void fraction in the catalyst bed. The three factors determining said linear velocity of the gas stream are further explained below.

Firstly, said "flow rate of the gas stream" means the flow rate (in cubic meters/second; $m^3/s$) of the gas stream comprising oxygen and hydrocarbons, said hydrocarbon including the alkane and/or alkene, and optionally an inert gas. In case two or more gas streams are fed to the reactor, for example one gas stream comprising oxygen and another gas stream comprising an alkane such as ethane, then said "flow rate of the gas stream" means the sum of the flow rates of all of the gas streams fed to the reactor. This flow rate is measured at the entrance of the catalyst bed, which is the position inside the reactor at which the gas stream comprising oxygen and the alkane and/or alkene is contacted with catalyst particles for the first time. This implies for example that said flow rate is measured at the temperature and pressure that exist at said entrance of the catalyst bed.

Secondly, said "cross-sectional surface area of the reactor" (in square meters; $m^2$) means the surface area of the cross-section of the reactor excluding that portion of said surface area which is taken up by the wall of the reactor. Said cross-section is obtained by (imaginarily) cross-secting the reactor in a direction which is perpendicular to the direction of the reactor length. Said cross-section is the cross-section at the entrance of the catalyst bed. For example, in a case wherein the reactor is cylindrical, because of which the cross-section is circular, said "cross-sectional surface area of the reactor" is determined by the formula [pi*d*d]/4, wherein "pi" is a dimensionless constant having a value of about 3.14, and "d" is the inner diameter (in meters) of the cylindrical reactor.

Thirdly, said "void fraction in the catalyst bed" is defined as follows: void fraction in the catalyst bed (dimensionless) =volume of voids in the catalyst bed/total volume of the catalyst bed. Said "volume of voids in the catalyst bed" consists of the volume of voids between the particles in the catalyst bed and does not include the volume of any pores present inside those particles, as would be present inside porous particles.

In the present specification, the term "voids" is used to indicate the voids which are present between the (catalyst) particles, whereas the term "pores" is used to indicate any voids (the "pores") which may be present inside the (catalyst) particles as in porous (catalyst) particles.

Said "total volume of the catalyst bed" means the total volume of the catalyst particles, any inert particles and the voids between the particles. For example, in a case wherein the reactor is cylindrical, said "total volume of the catalyst bed" may be determined as follows. Firstly, the height of the catalyst bed inside the rector is determined by measuring the height of the empty part of the reactor not containing the catalyst bed and the height of the empty part of the reactor containing the catalyst bed. The difference between the latter 2 heights is the height of the catalyst bed inside the rector. Secondly, using the latter height and the cross-sectional surface area of the reactor, in that portion of the reactor where the catalyst bed is present, said "total volume of the catalyst bed" can be measured.

Said "void fraction in the catalyst bed" is defined by the following quotient: density of the particles/density of the catalyst bed. As discussed above, said particles comprise catalyst particles and any inert particles.

Said "density of the catalyst bed" may be determined as follows. Firstly, the total volume of the catalyst bed is determined as described above. Secondly, the total weight of the catalyst bed is divided by said total volume of the catalyst bed, resulting in the density of the catalyst bed.

Said "density of the particles" takes into account the presence of any pores inside the particles. Said "density of the particles" is defined by the following quotient: total weight of the particles/total volume of the particles. In said "total volume of the particles", the volume of any pores present inside the (porous) particles is included and the volume of the voids which are present between the particles is excluded.

Said "density of the particles" may be determined by any suitable method known to the skilled person. A suitable method comprises contacting the particulate catalyst (catalyst particles), which particulate catalyst is preferably porous, with mercury. In this method, the above-mentioned "total volume of the particles", including the volume of any pores present inside the (porous) particles and excluding the volume of the voids which are present between the particles, is determined. In this method, the pressure is chosen such that said pores are not filled with mercury whereas said voids are filled with mercury when the porous, particulate catalyst is contacted with mercury. Suitably, said pressure is atmospheric pressure. This method involves measuring, at said pressure, the volume of mercury filling a container wherein no particulate catalyst has been placed and measuring the volume of mercury filling the same container wherein a particulate catalyst of a given weight has been placed. The difference between these two volumes is the above-mentioned "total volume of the particles". Such method is described by Clyde Orr, Jr. in "Application of Mercury Penetration to Materials Analysis", Powder Technology, 3 (1969/70), pages 117-123, the disclosure of which is incorporated herein by reference, more in particular the section "Density" at page 121.

Thus, in the present invention, the linear velocity of the gas stream as defined above is expressed as $m^3$ gas/$m^2$ voids/second, which is the volume of the gas that passes 1 $m^2$ of voids in the catalyst bed per second. As mentioned above, by said "voids" only reference is made to the voids which are present between the (catalyst) particles and not to any pores inside those particles.

In the present invention, the linear velocity of the gas stream comprising oxygen and the alkane and/or alkene is at least 10 cm/sec. Preferably, said linear velocity is in the range of from 10 to 500 cm/sec, more preferably 20 to 300 cm/sec, more preferably 30 to 200 cm/sec, more preferably 35 to 150 cm/sec, most preferably 40 to 120 cm/sec. Further, preferably, said linear velocity is at least 15 cm/sec, more preferably at least 20 cm/sec, more preferably at least 25 cm/sec, more preferably at least 30 cm/sec, more preferably at least 35 cm/sec, more preferably at least 40 cm/sec, more preferably at least 45 cm/sec, more preferably at least 50 cm/sec, more preferably at least 55 cm/sec, more preferably at least 60 cm/sec, more preferably at least 65 cm/sec, most preferably at least 70 cm/sec. Still further, preferably, said linear velocity is at most 500 cm/sec, more preferably at most 450 cm/sec, more preferably at most 400 cm/sec, more preferably at most 350 cm/sec, more preferably at most 300 cm/sec, more preferably at most 250 cm/sec, more preferably at most 200 cm/sec, more preferably at most 175 cm/sec, more preferably at most 150 cm/sec, more preferably at most 140 cm/sec, more preferably at most 130 cm/sec, more preferably at most 120 cm/sec, more preferably at most 110 cm/sec, most preferably at most 100 cm/sec.

In the present invention, one gas stream comprising oxygen and the alkane and/or alkene may be fed to the reactor. Alternatively, two or more gas streams may be fed to the reactor, which gas streams form a combined gas stream inside the reactor. For example, one gas stream comprising oxygen and another gas stream comprising an alkane, such as ethane, may be fed to the reactor separately. Said one gas stream or multiple gas streams may additionally comprise an inert gas, as further described below.

Preferably, in the alkane oxidative dehydrogenation process of the present invention, the alkane containing 2 to 6 carbon atoms is a linear alkane in which case said alkane may be selected from the group consisting of ethane, propane, butane, pentane and hexane. Further, preferably, said alkane contains 2 to 4 carbon atoms and is selected from the group consisting of ethane, propane and butane. More preferably, said alkane is ethane or propane. Most preferably, said alkane is ethane.

Further, preferably, in the alkene oxidation process of the present invention, the alkene containing 2 to 6 carbon atoms is a linear alkene in which case said alkene may be selected from the group consisting of ethylene, propylene, butene, pentene and hexene. Further, preferably, said alkene contains 2 to 4 carbon atoms and is selected from the group consisting of ethylene, propylene and butene. More preferably, said alkene is ethylene or propylene.

The product of said alkane oxidative dehydrogenation process may comprise the dehydrogenated equivalent of the alkane, that is to say the corresponding alkene. For example, in the case of ethane such product may comprise ethylene, in the case of propane such product may comprise propylene, and so on. Such dehydrogenated equivalent of the alkane is initially formed in said alkane oxidative dehydrogenation process. However, in said same process, said dehydrogenated equivalent may be further oxidized under the same conditions into the corresponding carboxylic acid which may or may not contain one or more unsaturated double carbon-carbon bonds. As mentioned above, it is preferred that the alkane containing 2 to 6 carbon atoms is ethane or propane. In the case of ethane, the product of said alkane oxidative dehydrogenation process may comprise ethylene and/or acetic acid, preferably ethylene. Further, in the case of propane, the product of said alkane oxidative dehydrogenation process may comprise propylene and/or acrylic acid, preferably acrylic acid.

The product of said alkene oxidation process comprises the oxidized equivalent of the alkene. Preferably, said oxidized equivalent of the alkene is the corresponding carboxylic acid. Said carboxylic acid may or may not contain one or more unsaturated double carbon-carbon bonds. As mentioned above, it is preferred that the alkene containing 2 to 6 carbon atoms is ethylene or propylene. In the case of ethylene, the product of said alkene oxidation process may comprise acetic acid. Further, in the case of propylene, the product of said alkene oxidation process may comprise acrylic acid.

The present alkane oxidative dehydrogenation process and/or alkene oxidation process comprises contacting a gas stream comprising oxygen ($O_2$) and the alkane and/or alkene with the mixed metal oxide catalyst. Said gas stream may be a combination of 2 gas streams being fed separately to the reator, one gas stream comprising the oxygen and one gas stream comprising the alkane and/or alkene. Additionally, said gas stream comprising oxygen and the alkane and/or alkene may contain an inert gas. Said inert gas may be selected from the group consisting of the noble gases and nitrogen ($N_2$). Preferably, the inert gas is nitrogen or argon, more preferably nitrogen. Said oxygen ($O_2$) is an oxidizing agent, thereby resulting in oxidative dehydrogenation of the alkane and/or oxidation of the alkene. Said oxygen may originate from any source, such as for example air.

Ranges for the molar ratio of oxygen to the alkane and/or alkene in said gas stream which are suitable, are of from 0.01 to 1, more suitably 0.05 to 0.5. Furthermore, in a preferred embodiment, said gas stream comprises 5 to 35 vol. % of oxygen, more suitably 15 to 25 vol. % of oxygen, and 40 to 80 vol. % of the alkane and/or alkene, more suitably 50 to 70 vol. % of the alkane and/or alkene, and less than 80 (0 to 80) vol. % of the above-mentioned inert gas, more suitably less than 50 (0 to 50) vol. % of said inert gas, more suitably 5 to 35 vol. % of said inert gas, most suitably 10 to 20 vol. % of said inert gas. In the context of the present invention, the components of said gas stream are to be selected in an overall amount not to exceed 100 vol. %.

Said ratio of oxygen to the alkane and/or alkene and said volume percentages for oxygen, the alkane and/or alkene and said inert gas are the ratio and volume percentages, respectively, at the entrance of the catalyst bed. Obviously, after entering the catalyst bed, at least part of the oxygen and alkane and/or alkene from the gas stream gets consumed.

In the present invention, the catalyst is a mixed metal oxide catalyst containing molybdenum, vanadium, niobium and optionally tellurium as the metals, which catalyst may have the following formula:

$$Mo_1V_aTe_bNb_cO_n$$

wherein:
   a, b, c and n represent the ratio of the molar amount of the element in question to the molar amount of molybdenum (Mo);
   a (for V) is from 0.01 to 1, preferably 0.05 to 0.60, more preferably 0.10 to 0.40, more preferably 0.20 to 0.35, most preferably 0.25 to 0.30;
   b (for Te) is 0 or is from >0 to 1, preferably 0.01 to 0.40, more preferably 0.05 to 0.30, more preferably 0.05 to 0.20, most preferably 0.09 to 0.15;
   c (for Nb) is from >0 to 1, preferably 0.01 to 0.40, more preferably 0.05 to 0.30, more preferably 0.10 to 0.25, most preferably 0.14 to 0.20; and
   n (for 0) is a number which is determined by the valency and frequency of elements other than oxygen.

Examples of oxydehydrogenation processes, including catalysts and other process conditions, are for example disclosed in above-mentioned U.S. Pat. No. 7,091,377, WO2003064035, US20040147393, WO2010096909 and US20100256432, the disclosures of which are herein incorporated by reference.

The amount of the catalyst in said process is not essential. Preferably, a catalytically effective amount of the catalyst is used, that is to say an amount sufficient to promote the alkane oxydehydrogenation and/or alkene oxidation reaction.

In the alkane oxidative dehydrogenation process and/or alkene oxidation process of the present invention, the gas hourly space velocity (GHSV; in $m^3$ gas/$m^3$ catalyst/hr) may typically be of from 100 to 50,000 $hr^{-1}$. Said GHSV is measured at standard temperature and pressure, namely 32° F. (0° C.) and 1 bara (100 kPa). In a preferred embodiment of the present invention, said GHSV is of from 2,500 to 25,000 $hr^{-1}$, more preferably of from 5,000 to 20,000 $hr^{-1}$, most preferably of from 7,500 to 15,000 $hr^{-1}$.

In the alkane oxidative dehydrogenation process and/or alkene oxidation process of the present invention, typical pressures are 0.1-20 bara (i.e. "bar absolute"), and typical temperatures are 100-600° C., suitably 200-500° C. Further, in a preferred embodiment of the present invention, the pressure is of from 0.1 to 15 bara, more preferably of from 0.5 to 10 bara, most preferably of from 1 to 5 bara. In a preferred embodiment of the present invention, the temperature is of from 300 to 500° C., more preferably of from 310 to 450° C., most preferably of from 320 to 420° C.

In general, the product stream comprises water in addition to the desired product. Water may easily be separated from said product stream, for example by cooling down the product stream from the reaction temperature to a lower temperature, for example room temperature, so that the water condenses and can then be separated from the product stream.

The invention is further illustrated by the following Examples.

EXAMPLES (A) Preparation of the Catalyst

A mixed metal oxide catalyst containing molybdenum (Mo), vanadium (V), niobium (Nb) and tellurium (Te) was prepared, for which catalyst the molar ratio of said 4 metals was $Mo_1V_{0.29}Nb_{0.17}Te_{0.12}$.

Two solutions were prepared. Solution 1 was obtained by dissolving 15.8 g of ammonium niobate oxalate and 4.0 g of anhydrous oxalic acid in 160 ml of water at room temperature. Solution 2 was prepared by dissolving 35.6 g of ammonium heptamolybdate, 6.9 g of ammonium metavanadate and 5.8 g of telluric acid ($Te(OH)_6$) in 200 ml of water at 70° C. 7.0 g of concentrated nitric acid was then added to solution 2. The 2 solutions were combined which yielded an orange gel-like precipitate. The mixture was evaporated to dryness with the aid of a rotating evaporator ("rotavap") at 50° C.

The dried material was further dried in static air at 120° C. for 16 hours, milled to a fine powder and then calcined in static air at a temperature of 300° C. for 5 hours. After the air calcination, the material was further calcined in a nitrogen (N$_2$) stream at 600° C. for 2 hours. Then the material was treated with an aqueous 5% oxalic acid solution at 80° C. and filtered and dried at 120° C.

The dried catalyst powder was pressed into pills which pills were then milled. The milled material was then sieved using a sieve having a mesh size of 40-80 mesh. The sieved material, having a size of 40-80 mesh and composed of porous catalyst particles, was then used in the ethane oxidative dehydrogenation experiments described below.

(B) Catalytic Oxidative Dehydrogenation of Ethane

Example 1: High Linear Gas Velocity

In Example 1, the catalyst thus prepared was used in a number of experiments involving ethane oxidative dehydrogenation within a small-scale testing unit comprising a vertically oriented, cylindrical, quartz reactor having an inner diameter of 2.2 mm. 694.3 mg of the catalyst were loaded in the reactor. The catalyst bed height was 11.4 cm.

In these experiments, a gas stream comprising 63 vol. % of ethane, 21 vol. % of oxygen (O$_2$) and 16 vol. % of nitrogen (N$_2$) was fed to the top of the reactor and then sent downwardly through the catalyst bed to the bottom of the reactor. Said gas stream was a combined gas stream comprising a flow of ethane having a rate of 3 Nl/hr, a flow of oxygen having a rate of 1 Nl/hr and a flow of nitrogen having a rate of 0.75 Nl/hr. "Nl" stands for "normal liter" as measured at standard temperature and pressure, namely 32° F. (0° C.) and 1 bara (100 kPa). Further, the gas hourly space velocity (GHSV) was 11.0×10$^3$ Nl/l catalyst/hr.

The temperature and pressure in the reactor for each of the experiments in Example 1 are shown in Table 1 below. In said table, the linear gas velocity is also shown. Said "linear gas velocity" has the meaning as given in the description preceding these Examples. The so-called "void fraction in the catalyst bed" was 40%.

The conversion of ethane and the product composition were measured with a gas chromatograph (GC) equipped with a thermal conductivity detector (TCD) and with another GC equipped with a flame ionization detector. The water from the reaction was trapped in a quench pot.

In Table 1 below, the experimental results (conversion of ethane and selectivity towards ethylene) for Example 1 are shown.

TABLE 1

| Exp. | Temperature (° C.) | Pressure (bara) | Linear gas velocity (cm/sec) | Conversion of ethane (%) | Selectivity to ethylene (%) |
|---|---|---|---|---|---|
| 1 | 336 | 2.3 | 85 | 10.4 | 96.6 |
| 2 | 346 | 2.3 | 87 | 14.7 | 95.8 |
| 3 | 368 | 2.4 | 90 | 26.9 | 94.3 |
| 4 | 378 | 2.4 | 91 | 34.8 | 93.3 |
| 5 | 390 | 2.4 | 93 | 44.0 | 92.2 |

Comparative Example 1: Low Linear Gas Velocity

In Comparative Example 1, the procedure of Example 1 was repeated with the following differences:
1. The reactor inner diameter was 12 mm.
2. 705.8 mg of the catalyst were used.
3. In addition to the catalyst particles, the catalyst bed also contained 3.8 ml of inert silicon carbide (SiC) particles having an average diameter of 0.1 mm.
4. The catalyst bed height was 3.7 cm.
5. At the top of the reactor, upstream of said catalyst bed, there was a bed (bed height=4.4 cm) only containing 5.0 ml of inert SiC particles having an average diameter of 0.2 mm.
6. The GHSV was 10.8×10$^3$ Nl/l catalyst/hr.
7. The linear gas velocity was lower, which is mentioned in Table 2 below.

The temperature and pressure in the reactor for each of the experiments in Comparative Example 1 are shown in Table 2 below. In said table, the linear gas velocity is also shown. Further, in said table, the experimental results (conversion of ethane and selectivity towards ethylene) for Comparative Example 1 are shown.

TABLE 2

| Exp. | Temperature (° C.) | Pressure (bara) | Linear gas velocity (cm/sec) | Conversion of ethane (%) | Selectivity to ethylene (%) |
|---|---|---|---|---|---|
| 1 | 355 | 2.2 | 3.3 | 24.1 | 93.4 |
| 2 | 365 | 2.2 | 3.3 | 29.0 | 93.1 |
| 3 | 374 | 2.2 | 3.3 | 34.6 | 92.2 |
| 4 | 382 | 2.2 | 3.3 | 38.6 | 92.0 |
| 5 | 382 | 2.2 | 3.3 | 37.7 | 92.1 |

In FIG. 1, a graph is shown wherein for each of the experiments from Example 1 and Comparative Example 1 (see Tables 1 and 2 above), data for the conversion of ethane (on the x-axis) and the selectivity towards ethylene (on the y-axis) are shown. Further, in FIG. 1, for each of Example 1 and Comparative Example 1, a straight "best fit" line is drawn connecting these conversion/selectivity data points.

Surprisingly, it appears from FIG. 1 that for the experiments of the present invention (Example 1) wherein the linear velocity of the gas stream comprising ethane and oxygen was above 10 cm/sec, the selectivity is higher at a given conversion or, conversely, the conversion is higher at a given selectivity, as compared to the comparative experiments (Comparative Example 1) wherein the linear velocity of said gas stream was below 10 cm/sec.

Comparative Example 2: Low Linear Gas Velocity

In Comparative Example 2, the procedure of Example 1 was repeated with the only difference that the linear gas velocity of Comparative Example 1 (see Table 2 above) was applied.

It was found that it was not possible to perform an experiment as there was question of an ignition (formation of carbon dioxide and water) wherein the temperature increased rapidly and uncontrollably such that the experiment had to be stopped. Therefore, no data for conversion and selectivity could be obtained.

Therefore, in addition to Comparative Example 1 showing that at a relatively low linear gas velocity only a lower selectivity and/or a lower conversion may disadvantageously be obtained, this Comparative Example 2 shows that at such low linear gas velocity it may even be that disadvantageously substantially no or less ethane oxidative dehydrogenation takes place, thereby producing substantially no or less ethylene but carbon dioxide and water instead.

That which is claimed is:

1. A process for the oxidative dehydrogenation of an alkane and wherein said alkane is ethane or propane, wherein a gas stream comprising oxygen and the alkane is contacted with a mixed metal oxide catalyst containing molybdenum, vanadium, niobium and optionally tellurium, and wherein the linear velocity of said gas stream is in the range of from 10 to 500 cm/sec.

2. The process according to claim 1, wherein a gas hourly space velocity is of from 2,500 to 25,000 hr$^{-1}$.

3. The process according to claim 1, wherein a pressure is of from 0.1 to 15 bara.

4. The process according to claim 1, wherein a temperature is of from 300 to 500° C.

* * * * *